United States Patent
Khan et al.

(10) Patent No.: US 9,650,608 B2
(45) Date of Patent: May 16, 2017

(54) ACTIVATING ADIPOSE-DERIVED STEM CELLS FOR TRANSPLANTATION

(71) Applicant: Medivet Pty Ltd., New South Wales (AU)

(72) Inventors: Shaneel Masood Khan, Blacktown (AU); Francis Edward Dwulet, Greenwood, IN (US); Andrew Gregory Breite, Indianapolis, IN (US)

(73) Assignee: MEDIVET AMERICA, LLC, Nicholasville, KY (US)

( * ) Notice: Subject to any disclaimer, the term of this patent is extended or adjusted under 35 U.S.C. 154(b) by 274 days.

(21) Appl. No.: 13/773,869

(22) Filed: Feb. 22, 2013

(65) Prior Publication Data

US 2015/0037289 A1 Feb. 5, 2015

(51) Int. Cl.
*A61K 35/28* (2015.01)
*C12N 5/0775* (2010.01)
*A61K 35/35* (2015.01)

(52) U.S. Cl.
CPC ............ *C12N 5/0667* (2013.01); *A61K 35/28* (2013.01); *A61K 35/35* (2013.01); *C12N 2502/115* (2013.01); *C12N 2509/00* (2013.01)

(58) Field of Classification Search
CPC . C12N 5/0667; C12N 2502/115; A61K 35/35
USPC ............................ 424/93.7; 435/2, 287.1, 381
See application file for complete search history.

(56) References Cited

U.S. PATENT DOCUMENTS

| | | | |
|---|---|---|---|
| 6,426,222 B1 | 7/2002 | Patat et al. | |
| 6,555,374 B1 | 4/2003 | Gimble et al. | |
| 6,777,231 B1 | 8/2004 | Katz et al. | |
| 7,078,232 B2 | 7/2006 | Konkle et al. | |
| 7,429,488 B2 | 9/2008 | Fraser et al. | |
| 7,514,075 B2 | 4/2009 | Hedrick et al. | |
| 7,531,355 B2 | 5/2009 | Rodriguez et al. | |
| 7,932,084 B2 | 4/2011 | Katz et al. | |
| 2001/0033834 A1 | 10/2001 | Wilkison et al. | |
| 2005/0153442 A1 | 7/2005 | Katz et al. | |
| 2006/0147430 A1 | 7/2006 | Sayre et al. | |
| 2008/0038236 A1 | 2/2008 | Gimble et al. | |
| 2010/0055074 A1 | 3/2010 | Romanczyk et al. | |
| 2010/0119492 A1 | 5/2010 | Hans et al. | |
| 2011/0008299 A1 | 1/2011 | Koullick et al. | |
| 2011/0060266 A1 | 3/2011 | Streeter et al. | |
| 2011/0206646 A1* | 8/2011 | Alfonso et al. | 424/93.7 |

OTHER PUBLICATIONS

World's First Affordable In-House Stem Cell Procedure Kit. Article [online]. MediVet, 2010 [retrieved on Jan. 29, 2015]. Retrieved from the Internet<URL:http://www.medivet.net.au/>.*

Adipose Derived Stem Cell Therapy. Article [online]. Packerland Veterinary Center, Ltd., 2004 [retrieved on Jan. 29, 2015]. Retrieved from the Internet: <URL:http://www.packerlandvet.com/dog/services/index.php?stemCellTherapy.php >.*

Liu et al., Injectable tissue-engineered bone composed of human adipose-derived stromal cells and platelet-rich plasma. Biomaterials, vol. 29 (online May 15, 2008) pp. 3338-3345.*

Information on EC 3.4.24.4-microbial metalloproteinases. Datasheet [online]. BRENDA, Jan. 2015 [retrieved on Feb. 6, 2015]. Retrieved from the Internet: <URL: http://www.brenda-enzymes.org/enzyme.php?ecno=3.4.24.27>.*

Information on EC 3.4.24.27-thermolysin. Datasheet [online]. BRENDA, Jan. 2015 [retrieved on Feb. 6, 2015]. Retrieved from the Internet: <URL: http://www.brenda-enzymes.org/enzyme.php?ecno=3.4.24.4>.*

Phosphate buffered saline. Datasheet [online]. Life Technologies, 2015 [retrieved on Feb. 7, 2015]. Retrieved from the Internet: <URL: http://www.lifetechnologies.com/us/en/home/technical-resources/media-formulation.160.html>.*

Bovine serum albumin. Datasheet [online]. Thermo Scientific, 2015 [retrieved on Feb. 7, 2015]. Retrieved from the Internet: <URL: http://www.thermoscientificbio.com/general-reagents-and-accessories/bovine-serum-albumin/>.*

* cited by examiner

Primary Examiner — Kara Johnson
(74) Attorney, Agent, or Firm — King & Schickli, PLLC (57) ABSTRACT

A method of preparing a stem cell preparation is provided. The method includes steps of collecting adipose tissue from a mammal, contacting that adipose tissue with an enzyme preparation to digest fat and connective tissue and preserve stem cells and collecting those stem cells. In addition a kit is provided for preparing a stem cell preparation.

16 Claims, 8 Drawing Sheets

ACTIVATING ADIPOSE-DERIVED STEM CELLS FOR TRANSPLANTATION

TECHNICAL FIELD

The present invention relates generally to methods of preparing stem cell preparations and to kits for preparing stem cell preparations used to treat bone, ligament, tendon or cartilage injury.

BACKGROUND

Musculoskeletal injuries and degenerative bone and joint diseases can be disabling. Those affected can suffer from reduced mobility and range of motion in addition to experiencing discomfort and pain. The joint of an animal refers generally to the location within the body where two bones are attached in close proximity. Joints are arranged to allow movement and provide structural support. In general, the two bones at the joint are separated by layers of articular cartilage on the opposing surfaces of the two joining bones with a synovial cavity containing synovial fluid between the layers of articular cartilage to provide lubrication for movement at the joint. The synovial cavity is further enclosed by a synovial lining surrounding the joint. Additional connective tissues including ligaments hold the bones at the joint together by attachment to the opposing bones. Similarly, tendons further connect muscle to one of the bones to allow for mechanical movement. Many injuries, conditions and diseases involve the joint and surrounding tissue.

Following injury or tissue damage, tissues may regenerate new functional cells either by division of existing functional cells or by differentiation of stem cells present in the tissue to form new functional cells. However, unwanted scar tissue may also form as part of the normal healing process which might impair regeneration and elasticity. Recently, stem cell transplants have been proposed as a treatment option for degeneration, damage or injury of the joint and other musculoskeletal tissues to promote tissue regeneration and restore function and performance while reducing pain and discomfort to the animal. These approaches are aimed at tipping the balance away from non-functional repair mechanisms and toward regeneration of functional cells. But, what are needed in the art are improved methods and compositions for isolating and activating particular stem cell fractions for the treatment of these diseases and conditions.

SUMMARY

In accordance with purposes described herein a method is provided for preparing a stem cell preparation used in treating a bone, ligament, tendon or cartilage injury in an animal such as a mammal. The method may be broadly described as including a step of collecting adipose tissue from a source animal. That adipose tissue includes fat, connective tissue and stem cells. In addition the method includes contacting the adipose tissue with an enzyme preparation that digests the fat and connective tissue while preserving the stem cells of the adipose tissue and then collecting those stem cells. The method may be characterized by the enzyme preparation including collagenase from *Clostridium histolyticum* and protease from *Bascillus thermoproteolyticus*.

In one embodiment the method further includes providing between 55-65 wt % collagenase from *Clostridium histolyticum* to 45-35 wt % protease from *Bascillus thermoproteolyticus* of the enzymes in the enzyme preparation. In addition the enzyme preparation includes a biologically inert protein stabilizer selected from a group of stabilizers consisting of a neutral salt, a sugar, sodium chloride, calcium chloride, glucose, fructose, sucrose, trehalose, mannose, dextrose and mixtures thereof.

That method may be further described as including collecting blood from the source animal and preparing a platelet rich plasma. The platelet rich plasma is prepared by separating the blood into a plasma layer and a red blood cell layer, collecting the plasma layer, separating the plasma layer into a platelet poor plasma layer and a platelet rich plasma layer and collecting the platelet rich plasma. In some embodiments the method further includes activating the platelet rich plasma by mixing the platelet rich plasma with an activating solution including, for example, a calcium chloride solution.

In accordance with an additional aspect, a method is provided for treating a mammal for a bone, ligament, tendon or cartilage injury. That method includes administering to a treatment animal a composition including a therapeutically effective amount of the stem cell preparation prepared by the current method. In one application the source animal and the treatment animal are the same animal. In some embodiments the animal is a mammal.

In accordance with yet another aspect, a kit is provided for preparing a stem cell preparation from adipose tissue. The kit may be broadly described as comprising a first sterile vessel of an enzyme preparation including collagenase from *Clostridium histolyticum* and protease from *Bascillus thermoproteolyticus*. In some embodiments the enzyme preparation includes between 55-65% collagenase from *Clostridium histolyticum* and 45-35% protease from *Bascillus thermoproteolyticus*. In some embodiments the kit includes a second sterile vessel of a plasma activation preparation. In some embodiments the plasma activation preparation comprises a calcium chloride solution.

BRIEF DESCRIPTION OF THE DRAWINGS

The accompanying drawings incorporated herein and forming a part of the specification, illustrate several aspects of the present invention and together with the description serve to explain certain principles of the invention. In the drawings.

Reference will now be made in detail to the present preferred embodiment of the invention, examples of which are illustrated in the accompanying drawings.

DETAILED DESCRIPTION

Where the definition of terms departs from the commonly used meaning of the term, applicant intends to utilize the definitions provided below, unless specifically indicated.

Stem cell—A stem cell must meet the following criteria: (1) ability of a clonal stem cell population to self-renew; (2) ability of a clonal stem cell population to generate a new, terminally differentiated cell type in vitro; and (3) ability of a clonal stem cell population to replace an absent terminally differentiated cell population when transplanted into an animal depleted of its own natural cells. (self-renew—numerous cell division in undiff state; potency—diff into diverse cell types).

"Adipose stem or stromal cells" refers to multipotent stromal cells or stem cells that originate from adipose tissue and are capable of self-renewal. By "adipose" is meant any fat tissue. The adipose tissue may be brown or white adipose tissue, derived from subcutaneous, omental/visceral, mammary, gonadal, or other adipose tissue site. In one embodiment, the adipose is subcutaneous white adipose tissue. Such cells may comprise a primary cell culture or an immortalized cell line. The adipose tissue may be from any organism having fat tissue.

Regenerative medicine provides a treatment option for wound healing as well as repair or restoration of damaged, injured, degenerative or diseased tissue. Regenerative medicine basically harnesses the ability of regenerative cells (e.g., stem cells and/or progenitor cells), to renew themselves and develop into more mature specialized cells, such as by administering these cells to sites of tissue damage, injury, disease or degeneration to promote healing or repair (i.e., encouraging regeneration of functional cells rather than non-functional repair mechanisms, such as scar formation).

Stem cells are present in the body of an animal throughout development. Stem cells may be found in embryos during early stages of development as well as in fetal and adult organs and tissues. Embryonic stem cells (or "ESCs") are generally undifferentiated and have the ability to become many different cell and tissue types within the body. Thus, it is believed that these cells may have tremendous potential for regenerative applications. However, because ESCs are necessarily derived from another individual (i.e., an embryo), there is a risk that a recipient's immune system will reject the new biological material, and immunosuppressive drugs may have limited effectiveness with these procedures and can create problems on their own. Moreover, transplanted ESCs have been shown to form tumors (e.g., teratomas), and the use of at least human ESCs may be obstructed by ethical concerns. Even in non-human animals, ESCs may be difficult to obtain and grow in large numbers.

Adult stem cells (or "ASCs") represent an alternative to the use of ESCs. ASCs reside quietly in many adult tissues, presumably waiting to respond to normal senescence, trauma or destructive disease processes so that they can heal the injured or diseased tissue and/or maintain normal tissue. Each individual carries a pool of ASCs that may have the potential to differentiate into many types of cells and tissues. These cells, unlike ESCs, may be used autologously to treat a diseased or injured tissue. ASC populations have been shown, for example, to be present in bone marrow, skin, fat, muscle, liver and brain. Thus, ASCs may have the potential for use in regenerative medicine. ASCs have been shown to have multiple regenerative actions including the ability to differentiate into mature functional cells, to produce trophic factors for tissue support and to modulate immune responses and inflammation.

However, the frequency and number of ASCs in many adult tissues is very low. These numbers of ASCs further tend to decline with age, contributing to reduced ability of tissues to repair and replenish themselves. In addition, extraction of ASCs from some tissues may require involved cell culturing steps, and it may take a considerable amount of time to isolate or concentrate the ASCs. Bone marrow transplantation provides a classic example where hematopoietic stem and progenitor cells are harvested from a donor and used to replenish the blood forming capacity of a recipient. But, the utility of bone marrow-derived stem cells for tissue engineering has been limited, due in part to low stem cell numbers and their tendency to differentiate. Induced pluripotent stem cells (iPS cells) from differentiated or partially differentiated adult cells have also been proposed recently, but these procedures generally require cellular alterations and/or genetic modification.

Accordingly, successful application of ASCs for regenerative medicine purposes may be greatly improved if the number and purity of progenitor or stem cells harvested from a tissue could be increased and if the length of time required to prepare, isolate, concentrate, etc., the ASC population is shortened. These regenerative techniques using ASCs might be further improved by preparing new cellular fractions containing ASCs that may have more favorable characteristics and/or by developing new methods for beneficially activating or triggering differentiation of ASCs before their administration to a recipient animal.

During development, early embryonic cells are considered to be largely totipotent and remain pluripotent through much of differentiation. There are three main germ layers or lineages formed during animal development. The ectoderm generally gives rise to skin and neural tissue, the endoderm generally forms the respiratory and digestive systems, and the mesoderm generally gives rise to cartilage, bone, fat, muscle, tendon and blood.

Mesenchymal stem cells (or "MSCs"), are a collection of cells mostly derived from the mesoderm that are present in diverse fetal and adult tissue types and may form part of the tissue stroma. These MSCs are considered multipotent and may become cells of many supportive tissues including bone (osteoblasts), cartilage (chondrocytes) and fat (adipocytes). MSCs are a distinct group of stem cells that are separate from hematopoietic stem cells. MSCs have been shown to have the ability to migrate to sites of injury and encourage tissue repair through proliferation and extracellular matrix production. Because of their ability to form structural tissue types, MSCs are proposed for use in regenerative medicine to promote healing, repair, restoration, etc., of damaged, injured, diseased, degenerative, etc., tissues.

Although present in many diverse tissue types, MSCs from bone marrow and adipose tissue may be the most promising for regenerative applications. Mesenchymal stem cells occur naturally in many tissues, but generally only in small amounts. As a result, it is difficult to isolate MSCs from tissue, and harvesting these cells from bone marrow is associated with a lot of pain to the donor. Recently, adipose tissue has been shown to be a rich source of MSCs. Unlike bone marrow and other tissues, adipose tissue is comparably easy to harvest in relatively large amounts (e.g., up to 1000 times the quantity of marrow) due to its abundance (especially in obese animals) and its ability to replenish itself. Thus, delays caused by culturing steps for expansion and to meet therapeutic thresholds are eliminated. Adipose-derived MSCs are also present in relatively much higher concentrations (e.g., 1000 times more stem cells than in marrow), and extraction of adipose tissue is generally less invasive due to its accessibility, less painful and safer compared to extraction of MSCs from other tissues. Furthermore, adipose-derived stem cells (AD-SCs) or adipose-derived mesenchymal stem cells (AD-MSCs) have been shown to possess the ability to generate multiple tissues, including bone, fat, cartilage, and muscle despite being in an "inactive" state when extracted. As with other ASCs, use of AD-MSCs does not require a second donor animal. Thus, adipose tissue is proposed as an optimal source for ASCs for use in regenerative medicine.

The method of preparing a stem cell preparation for treating a bone, ligament, tendon or cartilage injury in an animal such as a mammal comprises a number of steps. For purposes of the method an animal includes particularly a mammal such as a dog, cat or horse. The method may be broadly described as comprising the steps of: (a) collecting adipose tissue from a source animal where that adipose tissue includes fat, connective tissue and stem cells, (b) contacting the adipose tissue with an enzyme preparation that digests the fat and connective tissue while preserving the stem cells of the adipose tissue, and (c) collecting the stem cells. The method is particularly characterized by the enzyme preparation which includes collagenase from *Clostridium histolyticum* and protease from *Bascillus thermoproteolyticus*. In some embodiments the method includes providing between 55-65 wt % collagenase from *Clostridium histolyticum* and 45-35 wt % protease from *Bascillus thermoproteolyticus* of the enzymes in the enzyme preparation. In some embodiments the method includes providing about 60 wt % collagenase from *Clostridium histolyticum* and about 40 wt % protease from *Bascillus thermoproteolyticus* of the enzymes in the enzyme preparation. Still further the method includes providing a biologically inert protein stabilizer in the enzyme preparation. The protein stabilizer may comprise up to 70 or 80 wt % of the final enzyme preparation with the enzyme mixture of 35-45 wt % protease and 55-65 wt % comprising the other 20 to 30 wt % of the final enzyme preparation. That protein stabilizer may be selected from a group of stabilizers consisting of a neutral salt, a sugar, sodium chloride, calcium chloride, glucose, fructose, sucrose, trehalose, mannose, dextrose and mixtures thereof. The enzyme preparation may also include other additives such as glycylglycine and calcium chloride in small amounts.

The preparation of the enzyme preparation is further described in Example 1 presented below.

The method may be further described as including the collecting of blood from the source animal and preparing a platelet rich plasma from that blood. The platelet rich plasma is prepared in a two-step separation process. First the blood is separated into a plasma layer and a blood cell layer. This is followed by the collecting of the plasma layer. The collected plasma layer is then separated into a platelet poor plasma layer and a platelet rich plasma. This is followed by the collecting of the platelet rich plasma. In some embodiments the method then includes activating the platelet rich plasma by mixing the platelet rich plasma with an activating solution. Such an activating solution may include but is not limited to a calcium chloride solution having a concentration of between about 1.8% and about 3.8%. In some embodiments the method then includes mixing the platelet rich plasma with the collected stem cells in order to activate the stem cells and form the stem cell preparation.

Still further a method of treating an animal for bone, ligament, tendon or cartilage injury is provided. That method may be broadly described as comprising the administering to a treatment animal a composition including a therapeutically effective amount of the stem cell preparation disclosed in this document. In some particularly useful embodiments the source animal and the treatment animal are the same animal. In some embodiments the animal is a mammal. In some embodiments the animal is a dog. In some embodiments the animal is a cat. In some embodiments the animal is a horse.

In accordance with yet another aspect a kit is provided for preparing a stem cell preparation from adipose tissue of an animal. The kit may be broadly described as comprising a first sterile vessel of an enzyme preparation including collagenase from *Clostridium histolyticum* and protease from *Bascillus thermoproteolyticus*. In some particularly useful embodiments the enzyme preparation includes between 55-65 wt % collagenase from *Clostridium histolyticum* and 45-35 wt % protease from *Bascillus thermoproteolyticus* of the enzymes in the final preparation. In some useful embodiments the kit includes a second sterile vessel of a plasma activation preparation. In some embodiments that plasma activation preparation includes a calcium chloride solution.

A more detailed description of the preparation method, treatment method and kit follows.

Preparation Method

According to one broad aspect of the present invention, a new method, protocol or procedure is provided for extracting adipose-derived stem cells for transfer into an animal for treatment of joint or musculoskeletal tissue injury, disease, damage or degeneration. The present methods may provide for a particular sequence of purification steps, including various washes, centrifugation and digestion steps, to isolate, purify, produce, concentrate, etc., a unique stromal vascular fraction (SVF) containing AD-MSCs for therapeutic use. In addition to the AD-MSCs, the SVF produced by these procedures may also contain additional factors, peptides and other multipotent cells. According to some embodiments, the SVF containing AD-MSCs may be applied or administered autologously to the same animal. Alternatively, the SVF or AD-MSC cells may also be applied allogeneically or syngeneically. One advantage of administering cells or fractions autologously is safety in that the potential for immune responses and disease transmission may be reduced, minimized or eliminated. Also, because the ingredients may be obtained from the same animal being treated, it should be considered acceptable for use with performance animals, such as race horses. Another advantage of methods of the present invention is that all of the steps may be performed entirely in-house as part of a single, continuous process or procedure under the care or supervision of a doctor or veterinarian. Alternatively, however, the tissues and samples may be sent to an outside facility for extraction and processing.

AD-MSCs are believed to reside in a perivascular location in adipose tissue and may include and/or coexist with pericytes and endothelial cells. AD-MSCs may exert their regenerative potential through a number of activities. AD-MSCs have been shown to be immunomodulatory and anti-inflammatory, such as by immunosuppression, inhibition of T-cell proliferation, induction of regulatory lymphocytes and through apoptosis of CD8+ lymphocytes. Some of these effects may be mediated through the release or excretion of chemokines, cytokines and extracellular matrix proteins. MSCs may also enhance proliferation, migration and differentiation of endogenous stem cells in most tissues of the body, such as through cell-cell contact and mitochondrial exchange. Perhaps primarily, AD-MSCs may exert their regenerative and repair potential through their own differentiation into functional cells, such as by forming cartilage, chondrocytes, osteoblasts and/or improved tendon fiber reorganization. Other components of the SVF apart from the MSCs, which may include various factors and other multipotent cell types, may further enhance these features and provide additional benefits, including anti-inflammatory effects, biofactors and bioactive peptides and factors that contribute to reformation and architectural organization of tissues.

The International Society for Cellular Therapy has defined at least one set of minimal criteria for MSCs within a SVF from bone marrow or other tissues: The cells should adhere to plastic when cultured under standard conditions in a tissue culture flask. As exemplified in FIGS. 1a and 1b, the cells should be able to differentiate into osteoblasts (which may be confirmed by Alzarin Red staining), chondroblasts (which may be confirmed by Alcian blue staining) and adipocytes (which may be confirmed by Oil Red O staining) when cultured in differentiating conditions. When measured by flow cytometry, 95% or more of the cells should express: CD105, CD73, and CD90 and lack expression of: CD45, CD34, CD14, CD11b, CD79a or CD19; and 2% or less of the cells should have HLA class II. With flow cytometry, surface markers may be labeled with fluorescent markers and read with the use of a laser and electric field.

Figure 1A:
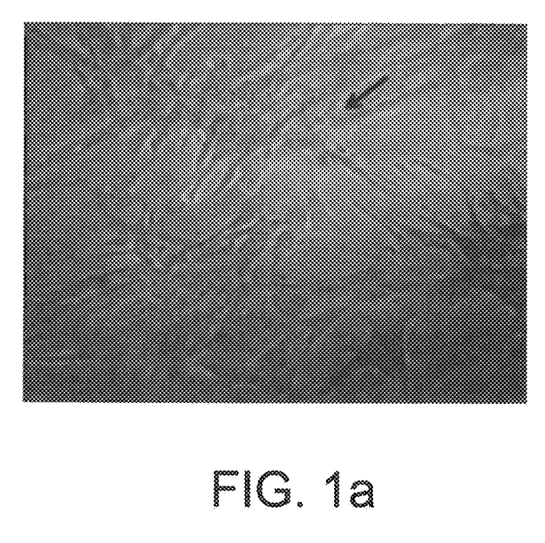
FIGS. 1a and 1b illustrates canine stem cell differentiation.
Figure 1B:
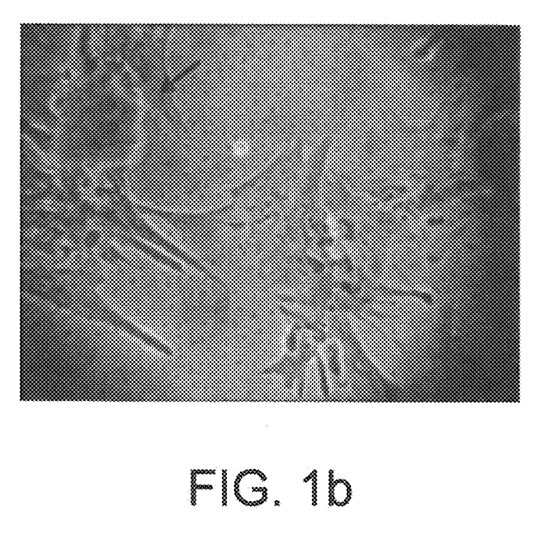

FIGS. 1a and 1b shows that AD-MSCs prepared according to methods described herein are capable of differentiating into multiple tissue types. For example, FIGS. 1a and 1b demonstrates osteoid-tissue formation from cultured AD-MSCs prepared according to present methods with Alzarin red S staining a pink color indicating bone mineral calcification (arrow). Osteocyte induction medium changed the cells from a fibroblastic appearance to a more cuboidal appearance, and were surrounded with an abundant matrix and formed mineralized nodules. FIGS. 1a and 1b also demonstrate adipose tissue formation from the AD-MSCs with Oil Red O staining. Cultures were treated with adipogenic induction media, resulting in abundant quantities of vacuoles observed in the cells after time. The Oil Red O staining for fat revealed that these vacuoles contained neutral lipids. DAPI staining is used to indicate the cell nucleus. FIGS. 1a and 1b further demonstrate cartilage tissue formation from the AD-MSCs with alcian blue staining. Cultures were treated with chondrogenic induction medium and were intensely stained with alcian blue, indicating a high content of mucopolysaccharides, which are associated with chondrocyte differentiation.

The SVF extracted, isolated, purified, concentrated, etc., by methods of the present invention may contain bone marrow stromal cells, follicular dendritic cells, and mesenchymal cells and/or one or more of the following as determined by FACS analysis: hematopoietic CD45 cells (e.g., about 9%), monocyte porogenitor CD14 cells (e.g., about 11%), early committed progenitor and mature granulocyte/monocyte CD13 cells (e.g., about 6%), hematopoietic CD90 stem cells (e.g., about 29%), early lymphohemopoietic stem and progenitor CD34/CD133 cells (e.g., about 7%), cells having endothelial-associated markers including CD31, CD105 and CD146, endothelial CD45/CD146 UEA-1 cells and CD271 cells (e.g., about 0.6%).

In addition, the SVF extracted, isolated, purified, concentrated, etc., by methods of the present invention may further contain many beneficial proteins that encourage bone formation, liver cell regeneration, nervous system regeneration, wound healing, vascular rebuilding, skin and damaged cell repair and/or re-growth. The SVF may contain one or more of the following: thymosine beta-4 (controls T cell maturation and helps damaged cells repair themselves), osteoclast-stimulating factor 1 (bone formation), caveolin-1 (liver regeneration and lipogenesis), ephrin-A1 (involved in the developing nervous system and erythropoietin), connective tissue growth factor (wound healing skin fibroblast stimulator, and endothelial angiogenesis), and transforming growth factor beta-2. The SVF may also contain various proteins present in the extracellular matrix of adipose tissue, such as laminin.

According to embodiments of the present invention, adipose tissue is extracted or removed from an animal to obtain stem cells. Through a series of steps, a stromal vascular fraction (SVF) containing AD-MSCs may be isolated, purified, concentrated, etc., from the extracted adipose tissue. All volumes and other amounts described herein with regard to embodiments of the present invention may be increased or decreased proportionally to alter yields, such as depending on the type and size of the animal to be treated. In general, sterile and/or aseptic procedures should always be used, including wearing gloves, masks and hairnets and disinfecting work surfaces.

According to some embodiments, before beginning the tissue extraction, various solutions may be prepared in anticipation of the procedure. A solution containing an enzyme preparation for digestion of tissues during the procedure may be prepared, such as by adding water or a solution to solubilize a powder or dry formulation of the enzyme(s) (perhaps with other ingredients) or to dilute a concentrated solution containing the enzyme(s). For example, a volume of sterile phosphate buffered solution (PBS) (e.g., about 1.0 ml) may be added to the enzyme(s) solution. The enzyme solution in combination with the one or more volumes of water and/or solution should be mixed well. The enzyme used in the preparation will generally include one or more enzymes for digesting the adipose tissue, such as proteases and the like (see below). Sterile procedures should always be used. Alternatively, the enzyme solution may have been previously prepared and stored, such as in a refrigerator or freezer.

An antibiotic solution may also be prepared if not previously prepared and stored for use during the extraction procedure. For example, the antibiotic solution may include gentamicin/Gentocin® (Schering). For example, a solution (e.g., about 0.5 ml) of the antibiotic (e.g., about 40 mg/ml) may be added to a solution (or a solution may be added to the antibiotic solution), such as by using a syringe and needle, and mixed well. The solution combined or added to the antibiotic solution may be sterile phosphate buffered solution (PBS) (e.g., about 19.5 ml). In addition, a volume of the antibiotic solution may be further diluted by addition of a volume of the antibiotic solution (e.g., about 5.0 ml) to another sterile phosphate buffered solution (PBS) (e.g., about 95 ml), such as by using a syringe and needle, and mixed well. Sterile procedures should always be used.

According to embodiments of the present invention, a platelet-rich plasma (PRP) may be used to "activate" or trigger differentiation of the SVF and/or other beneficial changes, such as proliferation and release or excretion of factors and extracellular matrix, to AD-MSCs when added to the SVF or (see below). The PRP may be prepared either in advance or in parallel with the adipose tissue extraction procedure. The PRP is prepared from the blood of an animal and may contain growth factors in addition to other beneficial biomolecules. Preferably, the PRP may be prepared from the same animal from which the adipose tissue is extracted, such that the PRP-treated SVF may be autologously administered or applied to the same animal.

According to these embodiments, a blood sample is first taken from the animal and placed into one or more tubes, such as blood collection tubes (e.g., ACD-A venous blood collection tubes). For example, the venous blood (e.g., about 15 ml or about 50 to 100 cc) collected from a donor or source animal may be placed into three ACD-A tubes (e.g., about 5 ml apiece), such as up to a mark or line on the tubes. This should generally be done under strict aseptic conditions. Once collected, the tubes may be inverted or mixed, such as about 8 times. The collection tube(s) containing the blood samples may be centrifuged at about 1000 g (i.e., about 2500 rpm) for about 4 minutes. After centrifugation, the top plasma layer is removed from each tube(s) and placed into a new tube (e.g., 15 ml tube), which may be done with the same syringe or pipette if transferred from more than one tube. Care should be taken to avoid drawing up the blood cell layer containing erythrocytes and a thin layer of white cells (buffy coat). To achieve this it may be advisable to avoid taking the last portion (e.g. about 5 mm) of plasma above the blood cell layer. Once the plasma layer is transferred to a new tube, it should be centrifuged again at about 1000 g (2500 rpm) for about eight minutes. At the end of this centrifugation step, there should be a platelet-containing pellet at the bottom of the tube. The top platelet-poor plasma should be removed and discarded. However, not all of the plasma above the pellet should be removed. Instead, a portion of the plasma (e.g., about 3 ml of plasma) should be left in the tube. This remaining portion of plasma should then be used to resuspend the platelet-rich pellet, which may be done using the same syringe or pipette used to remove and discard the plasma. This resuspension constitutes the platelet-rich plasma (PRP).

According to embodiments of the present invention, the PRP produced by this procedure may include one or more of the following components: platelet-derived growth factor (PDGF), TB-4 (may control T cell maturation and make damaged cells repair themselves), osteoclast-stimulating factor 1 (bone formation), caveolin-1 (liver regeneration and lipogenesis), Ephrin-A1 (involved in the developing nervous system and erythropoietin), connective tissue growth factor (CTGF; wound healing, skin fibroblast stimulator, endothelial angiogenesis), TGF-α and TGF-β (transforming growth factors alpha & beta), epidermal growth factor (EGF), fibroblast growth factor (FGF), insulin growth factor (IGF), platelet derived epidermal growth factor (PDEGF), platelet derived angiogenesis factor (PDAF), interleukin-8 (IL-8), tumor necrosis factor alpha (TNF-α), granulocyte macrophage colony stimulating factor (GM-CSF), keratinocyte growth factor (KGF), histamines, serotonin, ADP, thromboxane A2, and other vasoactive and chemotactic agents. There may also be high concentrations of leukocytes (neutrophils, eosinophils; microbicidal), wound macrophages and phagocytes (biological debridement), and platelets and native fibrinogen. Platelets may play a role in wound healing and provide hemostasis and release mediators to help modulate inflammatory responses and many of the above factors may be located in the alpha granuales of platelets. Albeit more concentrated, the PRP may contain factors including those listed above in roughly the same ratios or proportions as they exist in the body.

According to some embodiments, the PRP may itself be "activated" for later use by adding a volume of an activator solution such as a calcium chloride (CaCl2) solution to the PRP. For example, about 0.5 ml of CaCl solution may be added to the PRP, such as by using a syringe or pipette. This activator solution initiates the clotting cascade prior to the platelets being injected or placed in vivo allowing for growth factor release from the platelets. This expulsion of growth factors along with other bioactive molecules allows the growth factors to come into direct contact with additional signaling from the body of an animal receiving treatment. Activation results in rapid growth factor release with perhaps 90% of the prefabricated factors being released in ten minutes. Since many growth factors have short half-lives, this quick release provides significant benefit so long as the activated platelet rich plasma is used within about 240 minutes.

After mixing, the activated PRP should form a gel, such as in about 15-60 minutes. This reaction may be accelerated by placing in a 37° C. bath (shaking should preferably be avoided). Once this gel has formed, the tube or vial containing the PRP may be left at room temperature for a period of time, such as about 1-2 hours. During this time, the PRP will at least partially dissolve. However, the gelled PRP may not completely dissolve, and the rate of dissolution may depend on blood chemistry and overall health of the animal. In any case, there should generally be enough dissolved PRP for later use even if it is only partially dissolved. The activated PRP solution may be left aside in anticipation of its use during the SVF procedure. Again, the dissolution of this gel may be accelerated or sped up by placing in a 37° C. bath (shaking is optional). If at the end of this period, the gel is attached to the side of the tube, the tube may be vigorously jolted or tapped and allowed to dissolve for an additional short period of time or released by use of a spinal needle or sterile transfer pipette.

According to embodiments of the present invention, a method of processing adipose tissue surgically collected from an animal, such as a mammal, to produce, isolate, purify, fractionate, extract, concentrate, etc., a stromal vascular fraction (SVF) including adipose-derived stem cells, such as AD-MSCs, is provided. In a first step, an amount or volume of adipose tissue is removed from a donor or source animal, which may be the same as the recipient animal to be treated. The amount or volume of adipose tissue may depend on the type and size of animal and the amount, volume or number of SVF or AD-SCs desired for treatment. For example, the amount or volume of adipose tissue may depend on the body mass index and age of the donor, the time available for collection, the availability of accessible adipose tissue harvest sites, and the clinical purpose for which the tissue is being collected including the number of locations or joints to treat. The adipose tissue may be collected, obtained, extracted or removed according to any method known in the art. For example, adipose tissue may be removed from a patient by liposuction (syringe or power assisted) or by lipectomy, such as suction-assisted lipoplasty, ultrasound-assisted lipoplasty, and excisional lipectomy or combinations thereof. Adipose tissue is present in various accessible locations throughout the body of an animal and may be obtained, for example, from the thorax, inguinal or rump area of the animal. The animal may also receive an anesthetic for comfort.

According to embodiments wherein the adipose tissue is excised by lipectomy, the adipose tissue may be removed or excised and placed in a vessel or container (e.g., 70 ml container). According to some embodiments, the amount of adipose tissue excised and placed into a specimen container or jar may be from about 5 to about 20 grams of adipose tissue. The size of the specimen container should be large enough to allow the addition of solutions, such as at least about twice the volume as that of the tissue. The amount of stem cells obtained by the procedure is roughly proportional to the amount of tissue excised or removed.

In the case of adipose tissue removed by lipectomy, once the amount or volume of excised adipose tissue is placed into the specimen container or jar, the tissue should be finely cut or minced using scissors or other sharp utensil such that the tissue is divided into individual pieces of adipose tissue that are very small (e.g., about 2-4 mm apiece in size). Other tissues, such as muscle, should also be removed and discarded as much as possible. The fat tissue may now resemble a slurry. The finely cut adipose tissue may now be poured or transferred into a new tube, such as a 50 ml tube. Preferably, there should generally be about 5-20 ml of tissue. If there is extra tissue, amounts above 20 ml may be discarded.

To digest and break up the tissue and release the individual cells, an enzymatic step may be employed. The enzyme preparation used is available from MediVet America LLC under the trademark MEDISTEM. The enzyme preparation includes:

Ingredient 1: 60%:40% mixture of naturally derived, purified class I: class II collagenase from *Clostridium histolyticum*, with a total collagen degradation activity (CDA, as defined in Transplantation Proceedings 40:339, 2008) per bottle 0.08 grams of powder solute of 100,000±20,000 CDA units, Ingredient 2: Naturally derived, purified neutral protease from *Bascillus thermoproteolyticus* with a total neural protease activity (NPA as defined in Transplantation Proceeding 42:2052, 2010) of 100,000±20,000 NPA Units, and Ingredient 3: A biologically inert compound for its protein stabilization affect.

Such a biologically inert compound may include but is not limited to protein stabilizers consisting of a neutral salt, a sugar, sodium chloride, calcium chloride, glucose, fructose, sucrose, trehalose, mannose, dextrose and mixtures thereof. In one embodiment of the method, about 0.4 ml of the enzyme preparation is added to the adipose tissue using a sterile syringe and needle. Following this, an amount of an antimicrobial wash solution, such as phosphate buffered saline (PBS)+0.5 ml of 40 mg/ml Gentacin antimicrobial (e.g., about 2 ml), may be added, such as by syringe and needle, to raise the volume. An additional volume of solution, such as PBS, may be added, such as by syringe and needle, to raise the total volume to a desired amount, such as about 40 ml.

Following these steps, the contents may be mixed well by inverting the tube or container and placing in a 37° C. water bath, and the tube may also be shaken or agitated. Lower temperatures may also be used less preferably. The digestion reaction may then be allowed to incubate for a period of time, such as about 45 minutes. To keep the contents from settling to the bottom, the tube may be optionally removed every 10-15 minutes for agitating, mixing or inverting and placement back into the bath and a thin layer of white cells (buffy coat). To achieve this, it may be advisable to avoid taking the last portion (e.g., about 5 mm) of plasma above the blood cell layer. Once the plasma layer is transferred to a new tube, it should be centrifuged again at about 1000 g (2500 rpm) for about 8 minutes. (As an optional step, the solutions described above may be prepared during this longer centrifugation step in anticipation of the adipose extraction procedure to conserve time.)

According to embodiments of the present invention, after the enzymatic digestion reaction, a cell extraction medium may be added. According to some embodiments, the cell extraction medium may include an emulsifier or surfactant and may be lecithin-based (phosphatidyl choline), soy lecithin-based or glyceryl ester-based. For example, a volume of about 4 ml of a lecithin or soy lecithin-based solution may be added, such as by using a needle and syringe. Such a lecithin-based solution may be thick or viscous. Thus, it may be necessary to draw up the cell extraction solution slowly while moving the tip of the needle. Once the cell extraction medium is added to the digested adipose tissue, it may be incubated for a period of time (e.g., about 15 minutes) and may be mixed or inverted occasionally (e.g., at about 7 minutes). This incubation step may also be warmed, such as in a 37° C. bath.

Following this cell extraction step, the processed adipose tissue may be centrifuged, such as at about 800 g (about 2300 rpm), for a period of time, such as about 10 minutes. As a result of this step, three layers may be formed in the tube: a top yellow/clear layer; a white fibrous middle layer; and a red bottom layer having a cell pellet at the bottom of the tube (this pellet is the SVF containing the stem cells including AD-MSCs). Next, the bottom red layer containing the cell pellet may be removed and placed into a new container or tube. The red layer may be drawn up and transferred using a pipette, cannula and/or syringe, such as by inserting a cannula or pipette slowly down the side of the tube. All of the cell pellet and most of the red layer may be removed and transferred to a new container. Care should be taken to avoid taking the white fibrous layer because it may clog a filter later in the procedure. Thus, it may be advisable to stop drawing up the red layer when the white fibrous layer is near the bottom of the tube. The cannula or pipette tip may also be used to gently scrape pelleted cells off the surface of the tube. The red layer plus cells drawn up into the pipette, cannula and/or syringe may then be transferred or expelled into a new tube, such as a 50 ml tube. The rest of what remains of the adipose tissue preparation including the white fibrous layer and top yellow/clear layer may be discarded.

The stem cell-containing preparation produced by the steps above may be filtered to remove larger particles and debris. The pore size of the filter may be, for example, about 100 μm. This filtering step may also be done under vacuum to draw the fluid preparation by suction and/or gravity into another container or tube. The stem cell preparation may be transferred or poured onto a filter attached to another tube. However, it is preferred that contact with the environment is minimized, such as by directly attaching the sample tube containing the stem cell preparation to a new tube. For example, a Steriflip® filter unit (Millipore) may be attached to the tube containing the stem cell preparation. The Steriflip® filter unit may include a tube attached to a filter with a vacuum hookup or spigot for attaching a vacuum line or pump, such as a hand or motorized pump, to create suction into the new tube. A Steriflip® filter unit may be attached to the top of the sample tube containing the stem cell preparation and then inverted or flipped one time such that the new receiving tube is underneath and the stem cell preparation flows down onto the filter surface by gravity. The stem cell preparation may then be filtered by gravity and/or under vacuum pressure. The filtered stem cell preparation in the new container or tube (such as a 50 ml tube) may be capped, and the used filter and the old sample tube may be discarded.

Once the stem cell preparation is filtered into the new tube, it may be centrifuged at about 800 g (about 2300 rpm) for a period of time, such as about 10 minutes. As a result, a cell pellet of SVF containing the stem cells is again formed. The supernatant (the red liquid) may be removed using a pipette or syringe without disturbing the cell pellet. Attempts should be made to remove the brown fatty liquid on top of the supernatant. Approximately 1-3 ml of the supernatant above the pellet may be left behind, which may then be used to resuspend the pellet using the same pipette or syringe. To this resuspension, a wash volume of PBS+ Gentacin antimicrobial, such as about 20 ml, may be added to the tube and mixed well. The centrifugation step above is then repeated, and the supernatant (except for about 1-3 ml) is mostly removed and discarded. To this resuspension, a wash volume of PBS, such as about 12 ml, may be added to the tube and mixed well. It is important that the cell pellet be fully broken up in the resuspension for the next filtering step. However, some fibrous material may be present which is normal and will be removed in the next step.

This filtered and washed stem cell preparation may then be filtered again to remove additional debris and particles. The pore size of this second filter may be smaller, such as about 60 μm. This filtering step may also be done under vacuum to draw the fluid preparation by suction and/or gravity into another container or tube. The stem cell preparation may be transferred or poured onto a filter attached to another tube. However, it is preferred that contact with the environment is minimized, such as by directly attaching the sample tube containing the stem cell preparation to a new tube. For example, a Steriflip® filter unit (Millipore) may be attached to the tube containing the stem cell preparation. The Steriflip® filter unit may include a tube attached to a filter with a vacuum hookup or spigot for attaching a vacuum line or pump to create suction into the new tube. A Steriflip® filter unit may be attached to the top of the tube containing the stem cell preparation and then inverted or flipped one time such that the new receiving tube is underneath and the stem cell preparation flows down onto the filter surface by gravity. The stem cell preparation may then be filtered by gravity and/or under vacuum pressure. The filtered stem cell preparation in the new container or tube (such as a 50 ml tube) may be capped, and the used filter and the previous sample tube may be discarded.

The filtered stem cell preparation may then be transferred to a new tube, such as a 15 ml tube, such as by using a pipette or syringe, and this sample may then be centrifuged again at about 800 g (about 2300 rpm) for a period of time, such as about 10 minutes. Similarly to above, most of the supernatant may be removed and discarded. However, a small volume (e.g., about 0.5 ml) may be left behind with the pellet. Again, the cell pellet represents the SVF and may contain red and white cells in addition to stem cells.

According to embodiments of the present invention, a volume of PRP, which may be prepared as described above, may be added to, combined with, etc., the remaining volume containing the stem cell pellet to activate (e.g., trigger differentiation or cause other beneficial or favorable changes to) the SVF and/or AD-SCs due to the presence of active proteins and factors in the PRP. For example, a volume of the dissolved portion of the partially dissolved PRP described above may be added to the remaining volume containing the stem cell pellet, such as until the total volume reaches about 1-2 ml. The PRP preparation may have been left to dissolve while the above adipose extraction procedure was carried out. However, the volume of PRP added may depend on the number of locations or joints to be treated. When treating a joint, it should be kept in mind that (depending on which joint and the size of the animal) typically no greater than about 0.5 ml of the combined SVF/PRP preparation should be added to the joint of an animal. In general, the volume of PRP added may be about the same as the volume containing the stem cell pellet. Once the PRP is added, the SVF or stem cell pellet may then be resuspended, such as by using the pipette or syringe used to transfer the PRP. This resuspension may be mixed until it forms a single cell suspension.

According to some embodiments, the SVF and/or AD-SCs prepared as described herein, such as the combined SVF/PRP preparation described above, may be subjected to light stimulation or photobiostimulation to activate (e.g., trigger differentiation or cause other beneficial or favorable changes to) the SVF and/or AD-SCs. Light sensitive molecules and substances have been shown to be present in cells. Indeed, stem cells have been shown to be responsive or activated by light. Several molecules in fibroblasts have been shown to be photoacceptors, and fibroblasts have been shown to absorb light at various frequencies (e.g., 420, 445, 470, 560, 630, 690 and 730 nm). Five light frequency ranges (two in the green part of the spectrum, one in the yellow part of the spectrum and two in the red part of the spectrum) were found to stimulate AD-MSCs (e.g., cause proliferation), whereas frequencies in the blue part of the spectrum were found to inhibit these cells.

Using combinations of these wavelengths in the green, yellow and red parts of the light spectrum has stronger effects than individual wavelengths alone, and use of photostimulation in addition to PRP treatment further increases the stimulatory effect on AD-MSCs than either alone. The combination of exposure to PRP in addition to photostimulation greatly increases the amount of growth and/or proliferation of AD-SCs. In experiments, cultures of SVF and/or AD-SCs from a canine source either receiving PRP and photostimulation were compared after 8 days to those receiving no activation. The colony sizes for the activated cell cultures were significantly increased (e.g., about 19% in this example) over controls. The effects of both PRP and light stimulation were greater over time than either PRP or light activation alone. In these experiments, AD-SCs were cultured in DMEM medium with serum with or without PRP and light stimulated (where applicable) by exposure to the laser for about 30 minutes. In addition, activation caused by photostimulation was dependent on the wavelength of light used as discussed above with some combinations of light wavelengths resulting in even greater stimulation.

According to some embodiments, photostimulation at wavelength(s) within these ranges of the visual light spectrum may be used to stimulate the SVF and/or AD-MSCs preparation with or without further stimulation or activation by exposure of the SVF and/or AD-MSCs to PRP. Although the PRP is preferably added to the SVF prior to photostimulation, it may optionally be added after the light treatment. To photostimulate the SVF and/or AD-MSCs preparation (with or without the PRP having been added) may be transferred to a new tube or container, such as a cryotube (e.g., 2.5 ml cryotube). According to embodiments wherein the PRP is used, additional volume of PRP may be added to raise the volume if needed for effective light treatment. The tube containing the SVF and/or AD-MSCs may then be placed into the photobiostimulation unit, (which is basically an enclosed or mostly enclosed space for holding a sample and one or more light source(s), such as LED or laser lights, for stimulation of the sample in the path of the light). Once the tube and cells are placed in the unit the light source(s) in the unit may be turned on for a period of time, such as for about 20 minutes, to emit one or more of the five stimulatory wavelengths (two in the green part of the spectrum, one in the yellow part of the spectrum and two in the red part of the spectrum). See, e.g., PCT/CN2010/072041 filed Apr. 22, 2010, the entire contents and disclosures of which are incorporated herein by reference. After this step, the photostimulation step may be considered complete.

Following these procedures, the number of cells may be counted or quantified according to any method known in the art, such as by using a FACS, haemocytometer, microscope or suitable coulter counter. Cell types may also be identified and counted by type, and viable cells may be quantitated according to known methods. Based on these measurements, the number of cells may be calculated. These cell numbers may be used to determine the amount or volume of cells to use for treatment.

Following these procedures, the number of cells may be counted or quantified according to any method known in the art, such as by using a FACS, haemocytometer, microscope or suitable coulter counter. Cell types may also be identified and counted by type, and viable cells may be quantitated according to known methods. Based on these measurements, the number of cells may be calculated. These cell numbers may be used to determine the amount or volume of cells to use for treatment.

Treatment Method

According to another broad aspect of the present approach, a method of treating an animal, such as a mammal, is provided by administering a composition including a therapeutically effective amount of the stem cell preparation having the SVF and/or AD-MSCs prepared according to the procedures described herein, which may also have been stimulated or activated by PRP exposure. The activated stem cell preparation may then be applied or administered to an animal, which may be the same animal from which the PRP and/or SVF was derived (i.e., autologously applied in that the donor or source animal is the same as the recipient or treated animal). Alternatively, the activated SVF or stem cell preparation may be applied or administered to an animal, which is different than the animal from which one or both of the PRP and/or SVF was derived. In these less preferred cases, however, the PRP and/or SVF preparations should be derived from a closely related animal or species, such that the PRP and/or SVF are applied allogeneically or syngeneically to avoid or minimize adverse reactions.

According to embodiments of the present invention, an animal having or experiencing an injury or damaged, degenerative or diseased tissue may be treated or administered a composition comprising the stem cell preparation produced according to the methods described herein. Typically, the composition comprising the stem cell preparation may be applied or injected to the particular location(s) or site(s) of the injury or damaged, degenerative or diseased tissue. However, intravenous (i.v.) and/or intraperitoneal (i.p.) administration of these compositions is also envisioned especially for more systemic conditions or diseases or those involving multiple locations (e.g., multiple joints) in the body. Many injuries, conditions and diseases involve the joint and surrounding tissue including arthritis and osteoarthritis, arthropathy, ligament and tendon injuries, and bone fractures. Thus, embodiments of the present invention provide for local administration of compositions produced by present methods to the joint and/or surrounding tissue. However, administration of the present compositions may in some cases be counter-indicated for safety where there is active or recent remission of cancer or latent or overt infection.

According to some embodiments, an animal to be treated may be taken off all non-essentially medications for about 7-14 days including immune-suppressive drugs and steroids. Prior to and after treatment, the animal may be given NSAIDs. In those embodiments where the composition will be injected into the one or more of the location(s) or site(s), the stem cell preparation, in the form of a suspension may be drawn up into at least one syringe, such as a 1.0 ml or a 2.0 ml syringe, with the amount depending on the number of locations to be treated. In the case where injection is to be made into a joint, a maximum amount injected into the joint in the case of an animal about the size of a large dog or smaller may generally be about 0.5 ml, whereas the maximum amount injected may instead be about 0.2 ml for smaller animals (e.g., in the case of an animal about the size of a small dog). In the case of an animal corresponding to the size of a large dog or smaller, the maximum amount may alternatively be an amount derived from about 10 ml of adipose tissue or less. However, the amount or volume to be injected may vary and depend on the size and type of the animal as well as the particular tissue or joint to be treated. Indeed, the maximum amount injected into the joint of a large animal or tissue other than a joint may be greater than 0.5 ml. Although not usually preferred, compositions comprising SVF and/or AD-MSCs prepared according to methods described herein may be administered or injected in combination with one or more physiologically or pharmaceutically suitable carriers or solutions.

Following treatment with the SVF and/or AD-MSCs, the needle and treatment site may be flushed with an antibiotic, such as GENTOCIN® (gentamicin) (e.g., about 2 mg/kg body weight divided by the number of locations or joints to be treated). However, total GENTOCIN® (gentamicin) injected into the joint should generally not exceed about 25 mg or about 3 mg/kg body weight. In addition, the animal may continue to be treated with general antibiotics for a period of time thereafter, such as for about 5-7 days.

INJECTION EXAMPLES

Figure 2A:
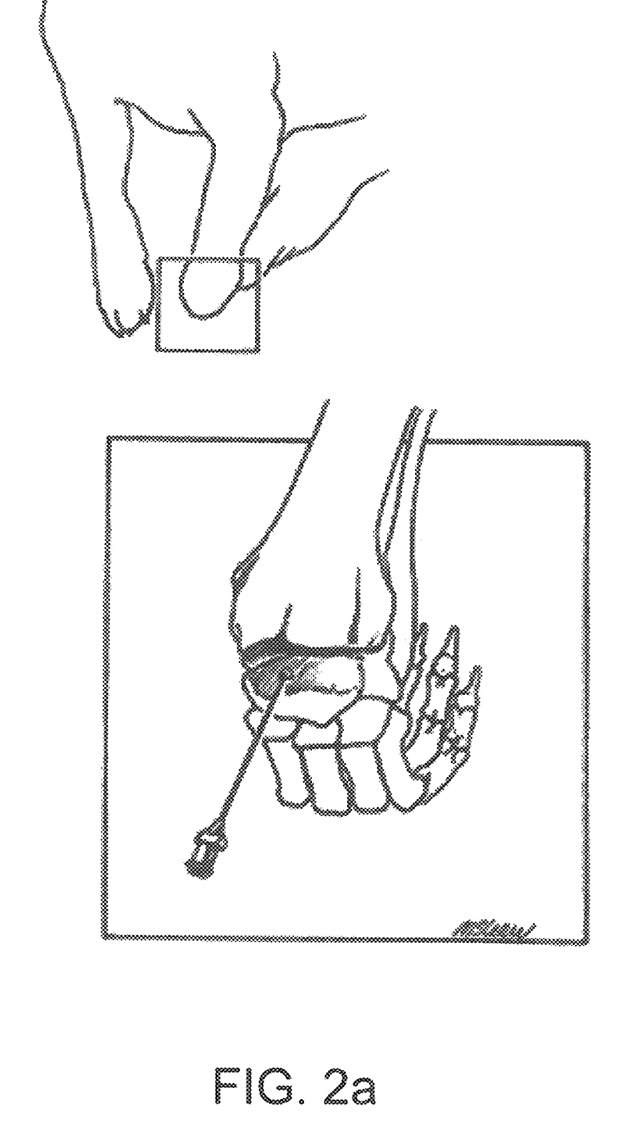
FIGS. 2a-2f illustrate possible injection sites for stem cell preparation.
Figure 2B:
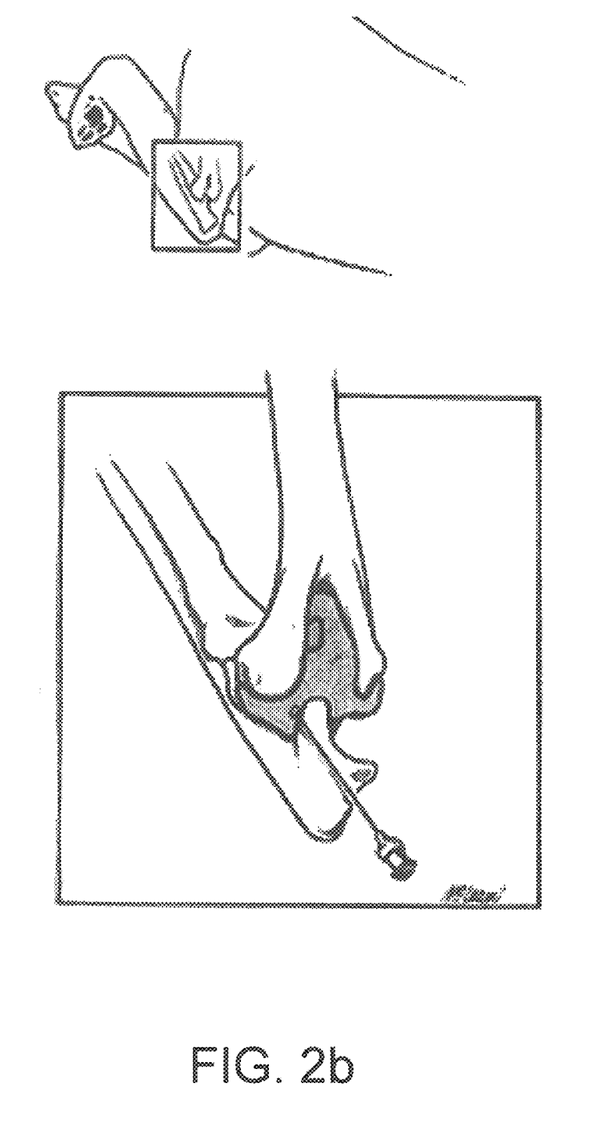
Figure 2C:
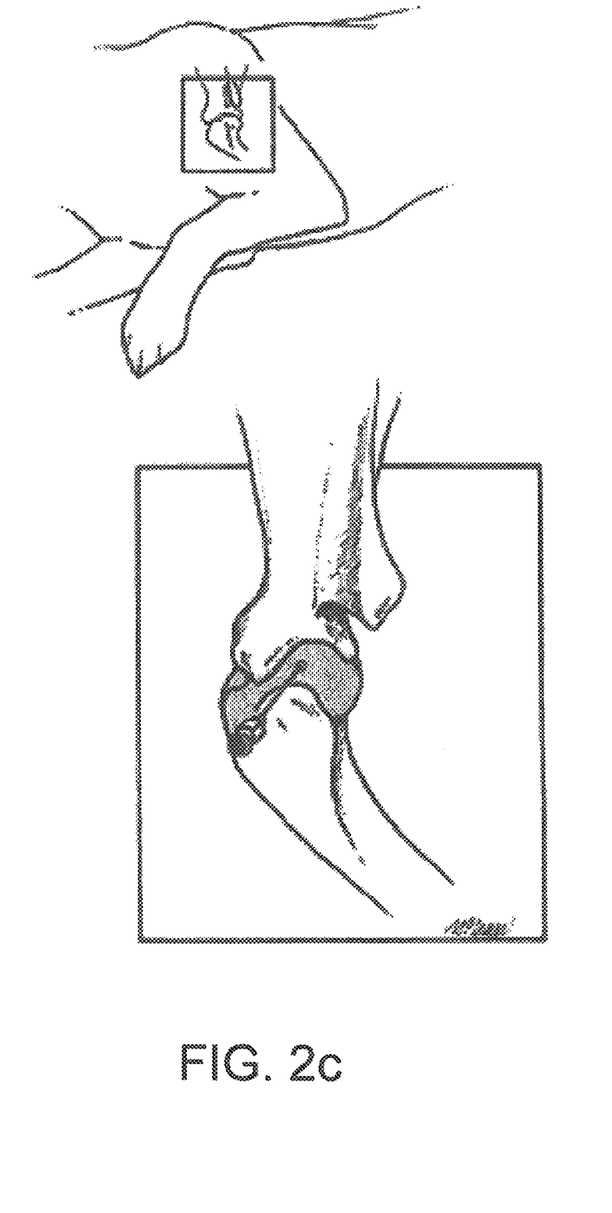
Figure 2D:
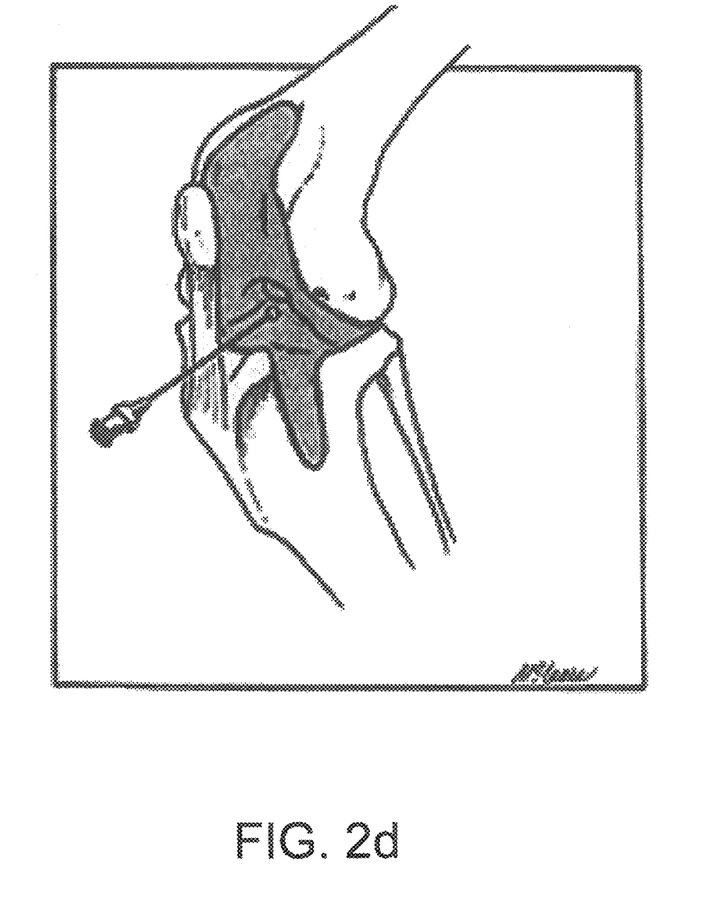

According to some embodiments, the composition comprising the stem cell preparation including SVF and/or AD-MSCs prepared according to methods described herein may be administered or injected into a joint of an animal (i.e., by intra-articular injection) according to any method known in the art. Such injection into a joint may be performed similarly to arthrocentesis or arthrodesis procedures for the respective joint. FIGS. 2a-2f provide some examples for injection into various joints of a canine. For example, FIG. 2a shows possible injection into the "wrist" of an animal (e.g., antebrachiocarpal injection). The joint may be flexed, and the needle may then be injected into the dorsal aspect of the joint just medial or lateral to the midsagittal plane. As shown in the example in FIG. 2b, the composition may be injected into the "elbow" of an animal. The joint may be in partial flexion, and the needle may penetrate the skin lateral and caudal to the anconeal process and the medial surface of the lateral humeral condyle. The example in FIG. 2c shows possible injection into the "shoulder" of an animal (e.g., scapulohumeral injection). The needle may enter the joint by passing proximal to the lateral aspect of the greater tubercle of the humerus, lateral to the supraglenoid tubercle of the scapula, and ventral to the acromion process of the scapula. FIG. 2d shows possible injection into the "knee" or stifle joint. The joint may be flexed sufficiently to cause tensing of the joint capsule. The needle may enter the joint either just medial or just lateral to the patellar ligament midway between the distal end of the patella and proximal articular surface of the tibia. Passing obliquely and caudally, the needle may be directed toward the intercondylar space of the distal femur. However, the needle may also be passed directly through the patellar ligament.

Figure 2E:
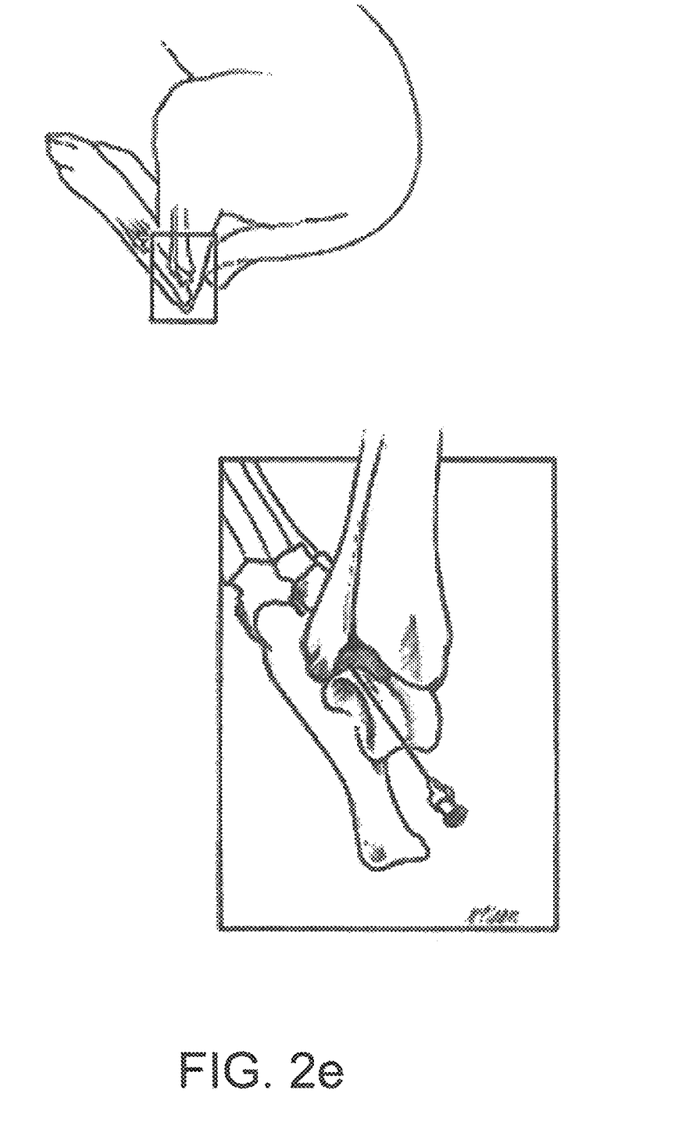
Figure 2F:
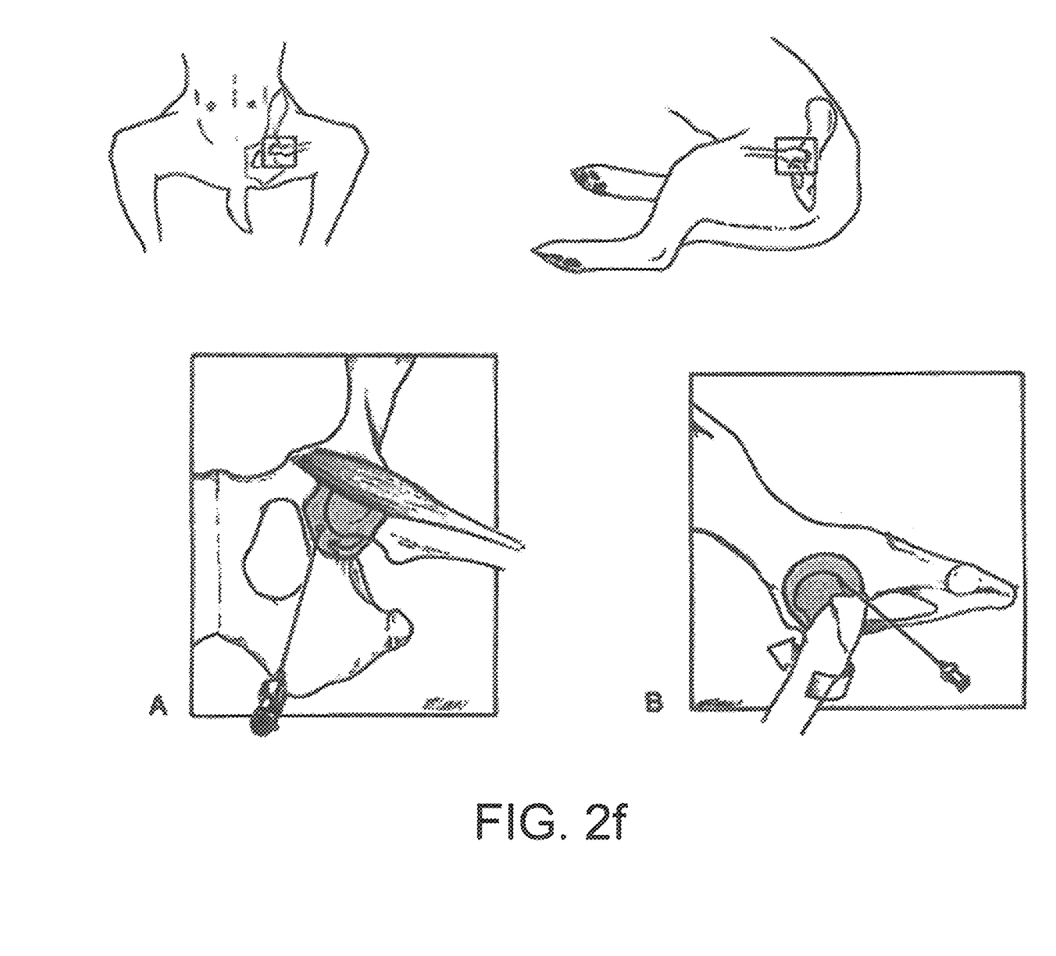

The example in FIG. 2e shows possible injection into the "ankle" joint of an animal (e.g., talocrural injection with caudal approach). The needle may enter the joint from its plantar-lateral aspect and is advanced in a dorsomedial and distal direction passing between the distal fibula and fibular tarsal bone, and joint flexion may facilitate entry into the joint. According to another example shown in FIG. 2f, the cells may be injected into the "hip" joint of an animal (e.g., coxofemoral injection). According to a first ventral approach as shown in the left panel, the needle may enter the ventral aspect of the joint just caudal to the body of the pectineus muscle. Directed at a 45° angle cranially and dorsally, the needle may pass lateral to the ventral acetabular rim and medial to the femoral head. According to a second lateral approach as shown in the right panel of FIG. 2f, the femur may be abducted slightly and rotated outward tensing the joint capsule, and the needle may pass just caudal and medial to the greater trochanter from a caudal to a cranial direction at an angle of approximately 45°.

Intravenous

According to embodiments of the present invention, a composition comprising SVF and/or AD-MSCs prepared according to methods described herein may be administered or injected by other more systemic means, such as by intravenous (i.v.) or intra-peritoneal (i.p.) injection. This may be done alone or in combination with administration of the composition to one or more locations or joints. Intravenously injected AD-MSCs have been shown to localize to damaged tissues, which may be mediated by chemotactic stress signals, such as stromal cell-derived factor 1 (SDF-1), hepatocyte growth factor (HGF), fractalkine and platelets. When injected intravenously, the composition may be administered or injected in combination with one or more physiologically or pharmaceutically suitable carriers or solutions. According to one embodiment, the composition may be combined with about 6-10 ml of warmed normal saline for intravenous administration, which may be administered over a period of time, such as about 20 minutes. In addition, the composition may be filtered before administration to remove large particles and debris prior to intravenous administration.

Adipose Stem Cell Preparation Kit

Figure 3:
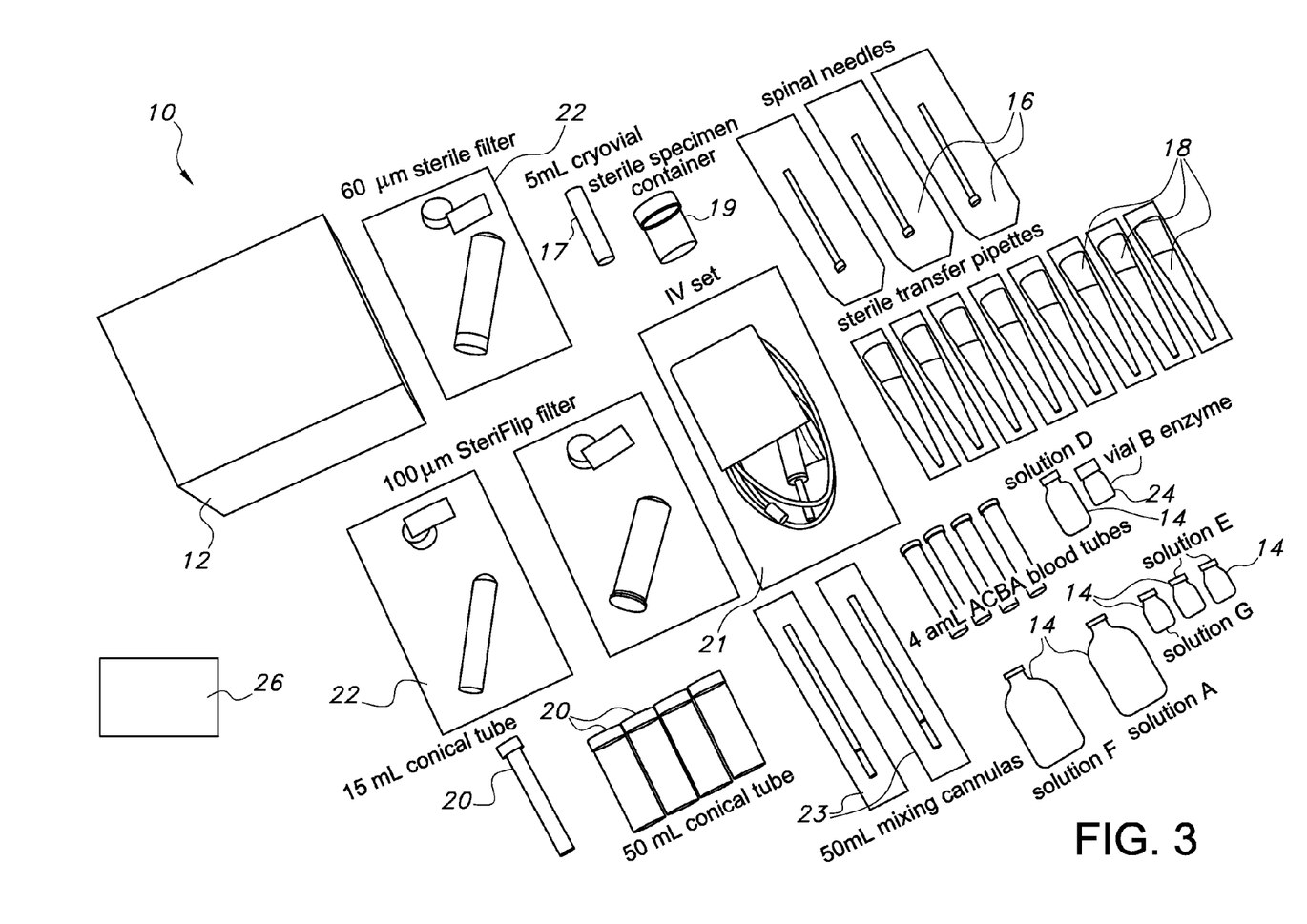
FIG. 3 illustrates a kit for preparing the stem cell preparation.

As best illustrated in FIG. 3, a kit 10 is provided for preparing a stem cell preparation of adipose tissue from a donor or source animal. The kit 10 comprises a box or container 12 including vessels 14 holding various solutions or preparations used in the method, needles 16, a cryovial 17, various pipettes 18, a sterile specimen container 19, various tubes 20, an IV set 21, filtering units 22, mixing cannulas 23, a vile of enzyme preparation 24 and instructions or directions 26 for completing the method described above. In one useful embodiment the kit includes the following.

I. Kit A

Solution A (e.g. PBS)—50 ml
Vial B—MEDISTEM enzyme preparation
Solution D (e.g. PBS+gentamicin)—19.5 ml
Solution E—MEDIVET cell extraction media 5.5 ml
Solution F (e.g. PBS+gentamicin)—95 ml
Solution G—ActiCell Activator Solution 2.5 ml (e.g. calcium chloride solution)
2×50 ml Polypropylene Conical Sterile Tube
1× Mixing Cannula
1× Steriflip 100 um Unit
1× Steriflip 60 um Unit
2×8.0 ml General Purpose Large Bulb Transfer Pipette
2×15 ml Polypropylene Conical Tube
1×2 ml Free Standing Cryotube
3×6 ml ACD Solution A Tubes
5× Graduated 3 ml Large Bulb Transfer Pipette
1× MEDIVET stem cell IV blood transfusion set
1×70 ml Polystyrene Sterile Container
Instructions In another useful embodiment the kit includes the following.

II. Kit B

Solution A (e.g. PBS)—95 ml
Vial B—MEDISTEM enzyme preparation
Solution D (e.g. PBS+gentamicin)—19.5 ml
Solution E—2× MEDIVET cell extraction media 5.5 ml
Solution F (e.g. PBS+gentamicin)—95 ml
Solution G—ActiCell Activator Solution 2.5 ml (e.g. calcium chloride solution)
4×50 ml Polypropylene Conical Sterile Tube
2 Mixing Cannula
2 Steriflip 100 um Unit
1 Steriflip 60 um Unit
5×8.0 ml General Purpose Large Bulb Transfer Pipette
1×15 ml Polypropylene Conical Tube
1×5 ml Free Standing Cryogenic vial
4×8.5 ml ACD Solution A Tubes
3× Graduated 3 ml Transfer Pipette
1× MEDIVET stem cell IV blood transfusion set
1×70 ml Polystyrene Sterile Container
3× Spinal needle
Instructions The following example generally describes the preparation of the enzyme preparation provided in the kit and used in the method.

Example 1

The enzyme preparation product is manufactured in four discrete set of operations listed below.

A. Collagenase Fermentation
B. Collagenase Purification
C. Thermolysin™ Purification
D. Blending of Enzyme Preparation A. Fermentation

*Clostridium histolyticum* (*C. histolyticum*) collagenases are obtained from *C. histolyticum* culture supernatants. These cells are obligate anaerobes and metabolize amino acids as an energy source.

During a production run a sample of cells are grown and expanded in a media formulated for cell growth until a sufficient cell volume is obtained to inoculate the production fermentor. A defined feed strategy is used for cell growth and enzyme synthesis. At the end of the fermentation the cells and cellular debris are removed from the spent media by passage through a 0.1 micron filter. The clarified supernatant contains the collagenase enzymes (Collagenase I (CI) and Collagenase II (CII)), along with at least two other proteases, unused fermentation media, as well as other secreted proteins and released soluble cell lysis products. After clarification the spent media is concentrated and diafiltered to remove the bulk of the remaining media and other low molecular weight components. When completed the concentrated supernatant is frozen for further processing.

B. Collagenase Purification

The concentrated crude collagenase preparation is purified using chromatographic processes as has been described previously in the literature (Dwulet, F E, et al. U.S. Pat. No. 5,989,888, 1999; Kurfürst M. U.S. Pat. No. 7,083,964 B2, 2006; Hoelke W, et al US Patent application US2011/0070622 A1, 2011). All chromatographic resins and the buffer agents used are chemically synthetic. The final products are purified CI and CII. These enzymes are characterized for their enzymatic activities and physical attributes. The final enzyme preparations are concentrated and stored as frozen liquids for further blending.

C. Thermolysin™ Purification

*Bacillus thermoproteolyticus* Neutral Protease (THERMOLYSIN™ (thermolase)) is a commercially available product from a manufacturer in Japan (cells are stored at the ATCC cell bank). The material is a partially purified preparation with lot to lot variability in specific activity and contamination profile. This material is further purified using a combined solubilization and ion exchange process to reduces the contaminate levels so that each preparation has, within the experimental error of the assay, the same lot to lot specific activity. The enzyme can be stored in bulk as a frozen liquid.

The blend of enzymes for the final enzyme preparation is composed of Collagenase I, Collagenase II and THERMOLYSIN™ (thermolase) blended in appropriate ratios to maximize the recovery of functional cells from animal adipose tissue (about 60 wt % collagenase and 40 wt % protease). The blended enzymes are then frozen and lyophilized. They may be subsequently mixed with a biologically inert protein stabilizer to make the final enzyme preparation for use in the disclosed method (e.g. 20-30 wt % enzyme mixture and 70-80 wt % biologically inert protein stabilizer).

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A method of preparing an adipose-derived mesenchymal stem cell preparation for treating a bone, ligament, tendon or cartilage injury in an animal, comprising:
   a. collecting adipose tissue from a source animal, said adipose tissue including fat, connective tissue and mesenchymal stem cells;
   b. contacting said adipose tissue with an enzyme preparation comprising 55-65 wt % collagenase from *Clostridium histolyticum* and 35-45 wt % protease from *Bascillus thermoproteolyticus* followed by incubation with a cell extraction medium;
   c. isolating mesenchymal stem cells after step (b);
   d. incubating isolated mesenchymal stem cells from step c with a platelet rich plasma derived from the source animal to form a mixture;
   e. photoactivating the mixture from step d; and
   f. administering the mixture to the animal.

2. The method of claim 1 further including providing a biologically inert protein stabilizer in said enzyme preparation wherein said biologically inert protein stabilizer is selected from a group of protein stabilizers consisting of a neutral salt, a sugar, sodium chloride, calcium chloride, glucose, fructose, sucrose, trehalose, mannose, dextrose mixtures thereof.

3. The method of claim 2, wherein d further comprises:
   (1) collecting blood from said source animal;
   (2) preparing the platelet rich plasma; and
   (3) mixing the platelet rich plasma from 2 with the isolated mesenchymal stem cells from c.

4. The method of claim 3 wherein said platelet rich plasma is prepared by separating said blood into a plasma layer and a blood cell layer, collecting said plasma layer, separating said plasma layer into a platelet poor plasma layer and a platelet rich plasma and collecting said platelet rich plasma.

5. The method of claim 4, further comprising activating said platelet rich plasma by mixing said platelet rich plasma with an activator solution including calcium chloride.

6. The method of claim 5, further comprising mixing said platelet rich plasma with the activator solution prior to f.

7. A method of treating an animal for a bone, ligament, tendon or cartilage injury, comprising:
   administering a treatment animal a composition including a therapeutically effective amount of said stem cell preparation of claim 6.

8. The method of claim 7 wherein said source animal is said treatment animal.

9. The method of claim 1, wherein said enzyme preparation comprises about 60 wt % collagenase from *Clostridium histolyticum* and about 40 wt % protease from *Bascillus thermoproteolyticus*.

10. The method of claim 9 further including providing a biologically inert protein stabilizer in said enzyme preparation wherein said biologically inert protein stabilizer is selected from a group of protein stabilizers consisting of a neutral salt, a sugar, sodium chloride, calcium chloride, glucose, fructose, sucrose, trehalose, mannose, dextrose and mixtures thereof.

11. The method of claim 10, wherein d further comprises:
   (1) collecting blood from said source animal;
   (2) preparing the platelet rich plasma; and
   (3) mixing the platelet rich plasma from 2 with the isolated mesenchymal stem cells from c.

12. The method of claim 11 wherein said platelet rich plasma is prepared by separating said blood into a plasma layer and a blood cell layer, collecting said plasma layer, separating said plasma layer into a platelet poor plasma layer and a platelet rich plasma and collecting said platelet rich plasma.

13. The method of claim 12, further comprising activating said platelet rich plasma by mixing said platelet rich plasma with an activator solution including calcium chloride.

14. The method of claim 13, further comprising mixing said platelet rich plasma with the activator solution prior to f.

15. A method of treating an animal for a bone, ligament, tendon or cartilage injury, comprising:
   administering to a treatment animal a composition including a therapeutically effective amount of said stem cell preparation of claim 14.

16. The method of claim 15 wherein said source animal is said treatment animal.

* * * * *